United States Patent [19]

Coleman et al.

[11] Patent Number: 5,403,309
[45] Date of Patent: Apr. 4, 1995

[54] CRYOSURGICAL ABLATION

[75] Inventors: Richard B. Coleman, Salisbury; Rudiger U. J. Pittrof, London; Simon R. Reeves, Warsash, all of United Kingdom

[73] Assignee: Spembly Medical Limited, Andover, United Kingdom

[21] Appl. No.: 99,202

[22] Filed: Jul. 29, 1993

[51] Int. Cl.⁶ .................................... A61B 17/36
[52] U.S. Cl. ......................... 606/20; 606/23; 607/104; 607/105; 604/113
[58] Field of Search .................... 606/20–26; 604/113; 607/105, 104

[56] References Cited

U.S. PATENT DOCUMENTS

| | | | |
|---|---|---|---|
| 3,174,481 | 3/1965 | Seaman | 607/105 |
| 3,398,738 | 8/1968 | Lamb et al. | 606/23 |
| 3,536,075 | 10/1970 | Thomas, Jr. | 606/23 |
| 3,924,628 | 12/1975 | Droegemuller | 606/21 |
| 4,275,734 | 6/1981 | Mitchiner | 606/23 |
| 4,846,177 | 7/1989 | Leonard | 604/113 X |
| 5,159,925 | 11/1992 | Neuwirth et al. | 607/105 |
| 5,242,390 | 9/1993 | Goldrath | 607/105 X |

FOREIGN PATENT DOCUMENTS

2244922 12/1991 United Kingdom ............. 606/23

*Primary Examiner*—Peter A. Aschenbrenner
*Attorney, Agent, or Firm*—Theresa M. Gillis

[57] ABSTRACT

A cryosurgical probe, insertable into a bodily cavity for performing cryosurgical ablation on the interior of the cavity, comprises a channel for introducing a heat-conducting liquid into the cavity, and a cooling element for cooling the heat-conducting liquid.

19 Claims, 6 Drawing Sheets

CRYOSURGICAL ABLATION

BACKGROUND OF THE INVENTION

1. Field of the Invention

This invention relates to cryosurgical ablation.

2. Description of the Prior Art

Cryosurgical ablation is a medical technique in which portions of bodily tissue are destroyed (ablated) by freezing. Known applications of this technique include the treatment of diseases of the eye, the cervix (the neck of the uterus) and the liver.

Known cryosurgical ablators comprise a probe having a hollow thermally conducting tip (e.g. a metal tip) which can be cooled by the introduction of a cryogenic liquid such as liquified nitrogen into the tip, or by the rapid expansion of a gas inside the tip (making use of the Joule-Thomson effect, described in the book "Equilibrium Thermodynamics" (C. J. Adkins, Cambridge University Press, 1983)). In operation, a surgeon touches the cooling tip onto an area of tissue to be destroyed, and the tip is then cooled to below the freezing point of water. This causes the aqueous content of tissue cells in contact with the cooling tip to freeze, which has the effect of killing those cells. A perceived advantage of the use of an apparatus of this type is that the ablation is localised at the tip of the probe, so the destruction of cells can be very selective.

Cryosurgical ablation has been suggested as a way of removing the lining of the uterus (the "endometrium") as a treatment for menorrhagia. Menorrhagia is condition suffered by many women in later life and involves excessive menstrual flow (i.e. heavy periods). The condition is caused by a deterioration of the endometrium, and is generally treated by removal of the entire uterus (a hysterectomy). The hysterectomy operation is a major surgical procedure and can be physically and emotionally debilitating for the women involved. Cryosurgical ablation of the endometrium would avoid the need for a hysterectomy, but so far has met with only limited success.

One reason for the poor success of previous attempts at cryosurgical ablation of the endometrium is that, in a uterus in which the procedure is required, the interior of the uterus has a very rough surface. This means that it is difficult to achieve contact between the cooling tip of a cryosurgical ablator and all parts of the endometrium. Also, the area of the interior surface of the uterus is large, which means that cryosurgical ablation of the endometrium is a lengthy procedure during which the surgeon may miss parts of the endometrium. In this respect, the selectivity of conventional cryosurgical ablation probes operates to reduce the success of cryosurgical ablation of large rough areas such as the endometrium.

It has been proposed in GB 1 332 181 that a cryogenic fluid (e.g. nitrogen or argon) should be dispensed directly onto the flesh to perform cryosurgical ablation. However, it would be potentially hazardous to spray such fluid onto the endometrium, because the cryogenic fluid could easily pass through the porous surface of the endometrium and form expanding bubbles of gas inside the flesh.

In U.S. Pat. No. 3,924,628 an expandable, flexible bladder is inserted into the uterus and is then filled with a cryogenic gas at low temperature. This technique has a number of disadvantages. It is not possible to tell whether the bladder is correctly positioned before the cryogenic gas is introduced. The bladder cannot provide uniform contact with the rough surface of the endometrium. If the bladder tears then cryogenic gas is dispensed onto the flesh, which can be hazardous to the patient's health. Also, the heat transfer between the bladder (which may be hardened with the cold) and the endometrium will be poor.

SUMMARY OF THE INVENTION

It is an object of the present invention to improve the cryosurgical ablation of the interior of a bodily cavity.

This invention provides a cryosurgical probe insertable into the interior of a bodily cavity for performing cryosurgical ablation on said interior of said cavity, said probe defining a channel for introducing a heat-conducting liquid into said cavity; and said probe comprising a cooling element for cooling said heat-conducting liquid in said cavity.

A probe according to the invention avoids the problems mentioned above of poor and localised thermal contact between the cooling element and the surface on which cryosurgical ablation is to be performed (e.g. the endometrium) by employing a heat-conducting liquid as an intermediary to conduct heat from the surface to the cooling element. The heat-conducting liquid can dilate the bodily cavity and assume the shape of the interior surface of the cavity (e.g. the uterus), so the cryosurgical ablation performed by the probe need not be hindered by a rough interior surface of the cavity. During the ablation operation, cryogenic fluid does not come into direct contact with the interior of the cavity.

Although other cooling mechanisms, such as the electrical Peltiet effect or the introduction of a cryogenic liquid such as liquefied nitrogen, may be used for cooling the cooling element, it is preferred that the cooling element is cooled by the expansion of a gas through a nozzle (the Joule-Thomson effect). To this end, it is preferred that the cooling element comprises a hollow chamber connectable to an exhaust vent and a gas nozzle connectable to a supply of gas at greater than atmospheric pressure.

The cooling element could be allowed to return to room (or body) temperature by means of heat conducted from surrounding objects. However, in a preferred embodiment the cooling element comprises a valve for selectively blocking the exhaust vent. This allows the cooling element to be re-heated quickly by means of the latent heat of condensation of gas supplied through the gas nozzle.

It is envisaged that a non-aqueous heat conducting liquid (such as medical paraffin) could be used. Such a liquid may have a freezing point below the temperature required for cryosurgical ablation, in which case it would not be necessary to freeze the liquid. However, in a preferred embodiment the heat-conducting liquid comprises an aqueous isotonic solution, the cooling element being operable to freeze the aqueous isotonic solution. Advantages of using an isotonic solution in this way are that the formation of ice around the cooling element during a surgical operation can be observed by the surgeon using a non-invasive ultrasound scanning device, and the known safety of the solution, should some of the solution be absorbed into the body.

In order that the surgeon can monitor the cooling process performed by the cooling element, it is preferred that the probe comprises means for detecting the temperature of the cooling element. Although many ways of sensing temperature are known, such as the use of thermistor sensors, in a preferred embodiment the means for detecting temperature comprises a thermocouple sensor in the cooling element.

As mentioned above, one application of a probe according to the invention is in cryosurgical ablation of the endometrium. Although the probe could be inserted into the uterus through an incision in the patient's abdomen, the operation can be made less invasive by inserting the probe through the patient's vagina. A preferred configuration of the probe for use in this way comprises a substantially cylindrical elongate body, with the cooling element comprising an elongate cooling tip attached to one end of the elongate body.

A probe which is inserted through the patient's vagina must dilate the cervix in order to reach the uterus. The dilation can be partially induced by drugs taken by the patient before insertion of the probe, but in order to assist in this dilation and in manoeuvring the probe in the uterine cavity, it is preferred that the principal axes of the elongate body and the cooling tip are not parallel (e.g. being offset by a small angle), and that the cooling tip is joined to the elongate body by a smoothly curved transition. Two further features assist in dilation of the cervix and in manoeuvring the probe in the uterine cavity: it is preferred that the distal end of the cooling tip has a rounded shape, and it is also preferred that the cooling tip is tapered and has a flattened cross section.

In order to prevent the outer surface of the elongate body from being cooled to the same low temperature as the cooling tip, it is preferred that the elongate body has a double-walled structure.

Although the heat-conducting liquid may be supplied from a source remote from the probe, it is preferred to give the surgeon direct control and tactile feedback over the introduction of the liquid into the cavity, by providing a probe comprising a syringe, connected to the channel, for supplying the heat-conducting liquid to the channel.

A probe using Joule-Thomson cooling as defined above may be employed in a cryosurgical ablation apparatus comprising means for supplying gas to the probe at greater than atmospheric pressure.

Although the valve for selectively blocking the exhaust vent may form part of the control unit, it is preferred that the probe comprises a handle portion, the handle portion comprising the valve for selectively blocking the exhaust vent.

The use of a control valve on the handle portion, to selectively block the exhaust vent, removes the requirement for a high pressure exhaust gas tube from the probe to the control unit. This means that it becomes possible to use a wide bore, low pressure tube. The use of a larger exhaust passage reduces the back pressure at the cooling element during a cooling operation; this in turn allows a more efficient cooling operation to take place and a lower temperature to be achieved.

As mentioned above, it is preferred that the cooling element back pressure is reduced by employing an inlet gas tube for supplying gas at greater titan atmospheric pressure to said gas nozzle; and an outlet gas tube for receiving gas from said exhaust vent; said inlet gas tube having a narrower bore than said outlet gas tube.

In order to reduce the force required to adjust the valve manually, it is preferred that the valve is a pressure-balancing valve.

Preferably a detent mechanism for maintaining said valve in a blocking position is employed. This can help to prevent unwanted cooling of the probe.

Viewed from another aspect this invention provides a method of performing cryosurgical ablation on the interior of a bodily cavity, said method comprising the steps of: introducing a heat-conducting liquid into said cavity; and cooling said heat-conducting liquid in said cavity.

BRIEF DESCRIPTION OF THE DRAWINGS

The above and other objects, features and advantages of the invention will be apparent from the following detailed description of illustrative embodiments which is to be read in connection with the accompanying drawings, in which.

DESCRIPTION OF THE PREFERRED EMBODIMENTS

Figure 1:
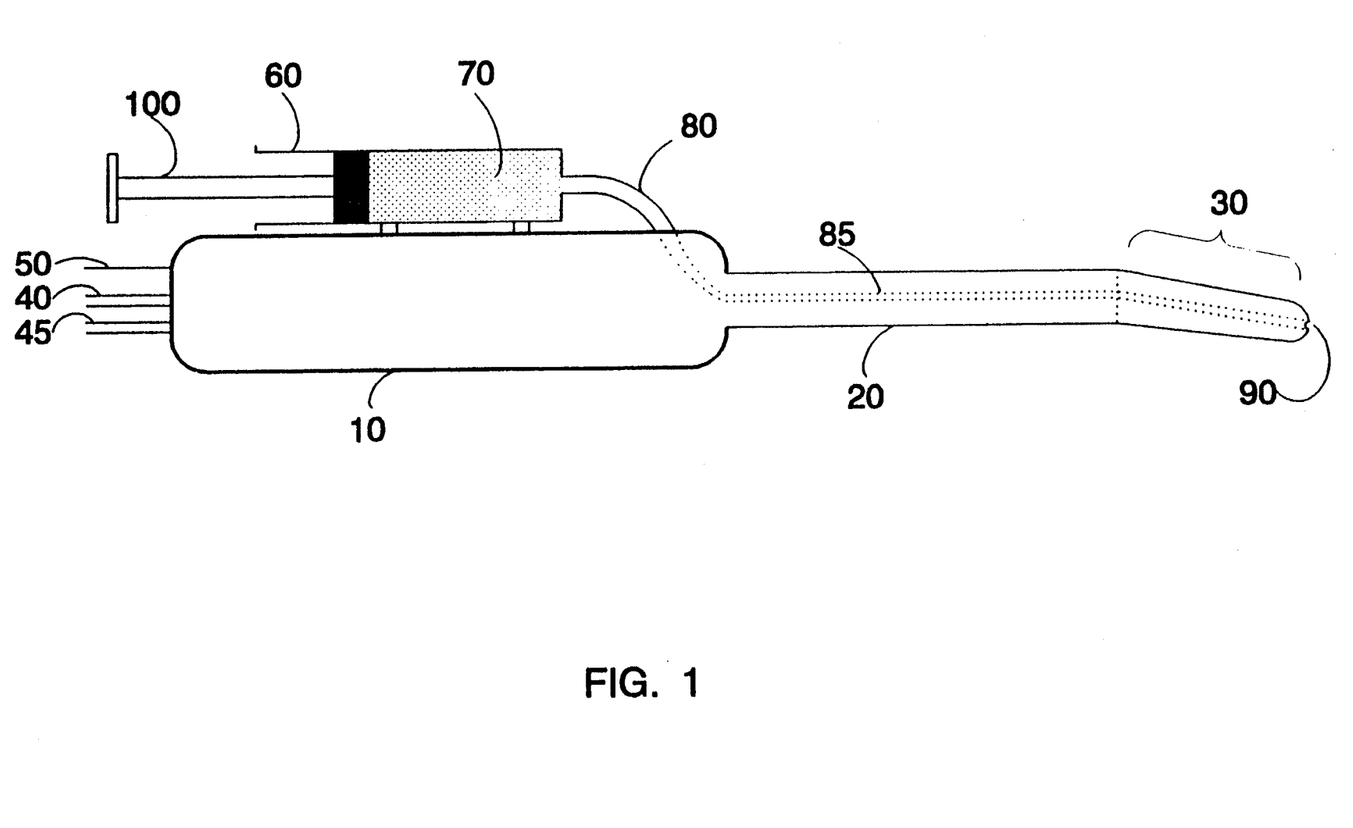
FIG. 1 is a schematic diagram of a cryosurgical probe according to the invention.

Referring now to FIG. 1, a cryosurgical probe according to the invention comprises a handle portion 10, a parallel sided cylindrical shaft 20 and a cooling tip 30. The cooling operation of the cooling tip 30 relies on the Joule-Thomson effect in which a high pressure gas (e.g. carbon dioxide), supplied through a gas inlet 40, is allowed suddenly to expand through a nozzle. The expanded gas exhausts through a gas outlet 45. The operation of the cooling tip 30 will be described in more detail with reference to FIG. 2 below. A thermocouple junction is mounted in the cooling tip 30 and connected by wires 50 to a control unit (not shown), so that the temperature of the cooling tip can be measured during a surgical operation.

A syringe 60 containing an isotonic solution 70 is mounted on the side of the handle portion 10. The outlet of the syringe is connected to a tube 80 which enters through the side of the handle portion 10 and communicates, via an axial channel 85 through the shaft 20, with an aperture 90 at the end of the cooling tip. This means that depression of a plunger 100 in the syringe 60 causes the isotonic solution 70 to pass through the tube 80, along the channel 85, and out of the aperture 90. The syringe 60 is positioned on the handle 10 so that, in operation, the plunger 100 can easily be operated by the surgeon.

As shown in FIG. 1, the longitudinal axis of the cooling tip 30 is at a slight angle to the longitudinal axis of the shaft 20, the cooling tip being joined to the shaft 20 by a smoothly curved transition. Also, the cooling tip is tapered and is slightly Flattened in cross section. In these respects the probe is shaped to follow the uterine cavity, in a similar manner to a so-called Hegar dilator. These features therefore assist a surgeon in manoeuvring the probe in a patient's uterine cavity.

Figure 2:
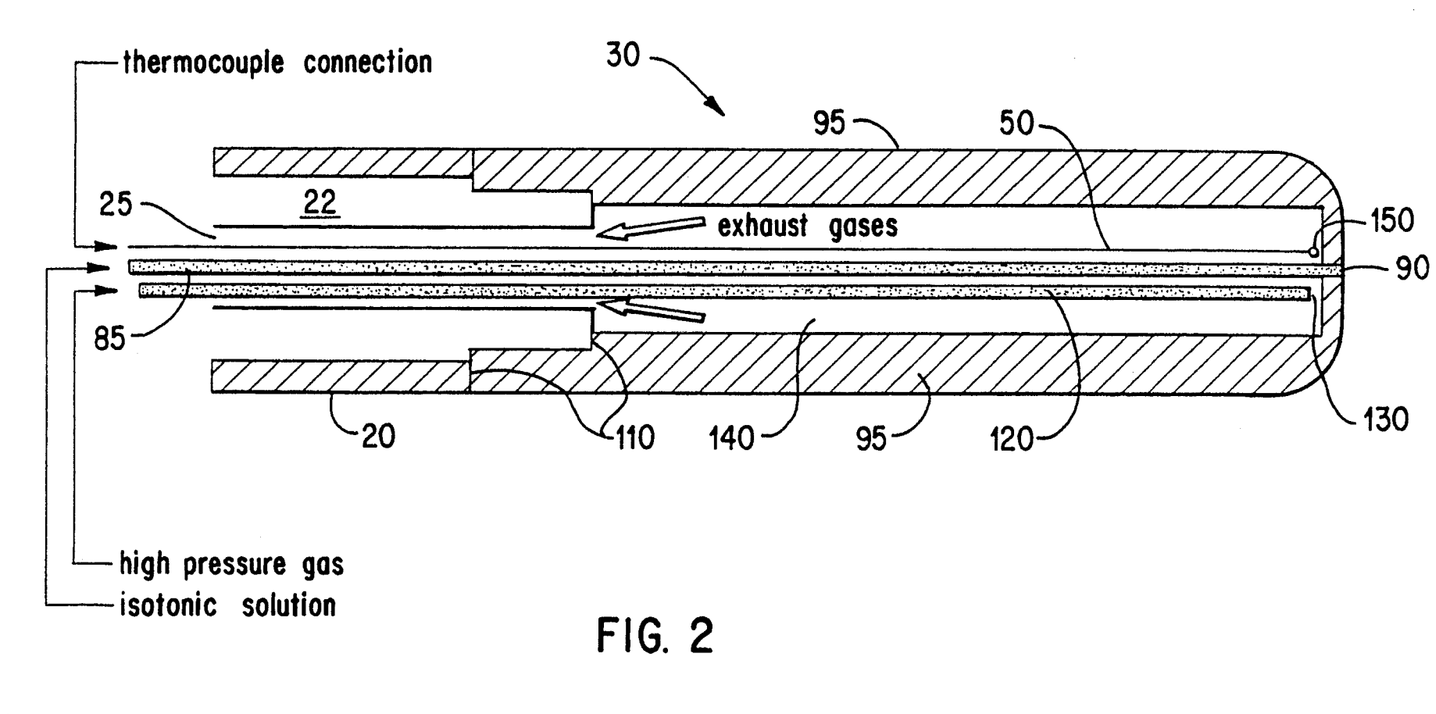
FIG. 2 is a schematic diagram of the cooling tip of the cryosurgical probe of FIG. 1.

FIG. 2 is a schematic diagram showing the operation of the cooling tip 30. The cooling tip 30 is hollow and has walls 95 formed of a material (e.g. coin silver) which has good thermal conduction properties and is able to withstand high gas pressures. The cooling tip 30 is connected by gas-tight joints 110 to the shaft 20. The shaft 20 has a double-walled structure, with the two walls being separated by an air gap or vacuum insulation gap 22. This prevents the outer surface of the shaft from being cooled to the same low temperature as the cooling tip. The inner wall of the shaft defines an inner chamber 25 which communicates with the gas outlet 45.

A high pressure gas supply tube 120 communicates with the gas inlet 40 and supplies high pressure gas to a nozzle 130. When it is required to cool the cooling tip, the gas is supplied through the high pressure gas supply tube 120 to the nozzle 130 at a pressure of about $5 \times 10^6$ Pascals (50 atmospheres). The high pressure gas is allowed to expand through the nozzle 130 into the hollow interior 140 of the cooling tip. Low pressure gas is then exhausted back through the inner chamber 25 of the shaft 20 and out of the gas outlet 45. The sudden expansion of the gas through the nozzle 130 operates according to the Joule-Thomson effect to cool the cooling tip 30, which can be cooled to several tens of degrees below the freezing point of water.

The temperature of the cooling tip is detected by a thermocouple 150 connected to the thermocouple wires 50.

As described above, the cooling tip 30 is cooled by the expansion of a high pressure gas through a nozzle into a low pressure region. The high pressure gas can also be used when appropriate, to provide sudden reheating of the cooling tip. If the exhaust of gas from the cooling tip is prevented by means of a valve (not shown), the gas pressure in the region 140 reaches the pressure of the gas supplied through the high pressure gas supply tube 120. namely $5 \times 10^6$ Pascals. The high pressure gas in the region 140 then condenses onto the interior surfaces of the cold walls 95 of the cooling tip. In doing so, the gas releases latent heat of condensation which has the effect of warming the walls of the cooling tip 30.

Figure 3:
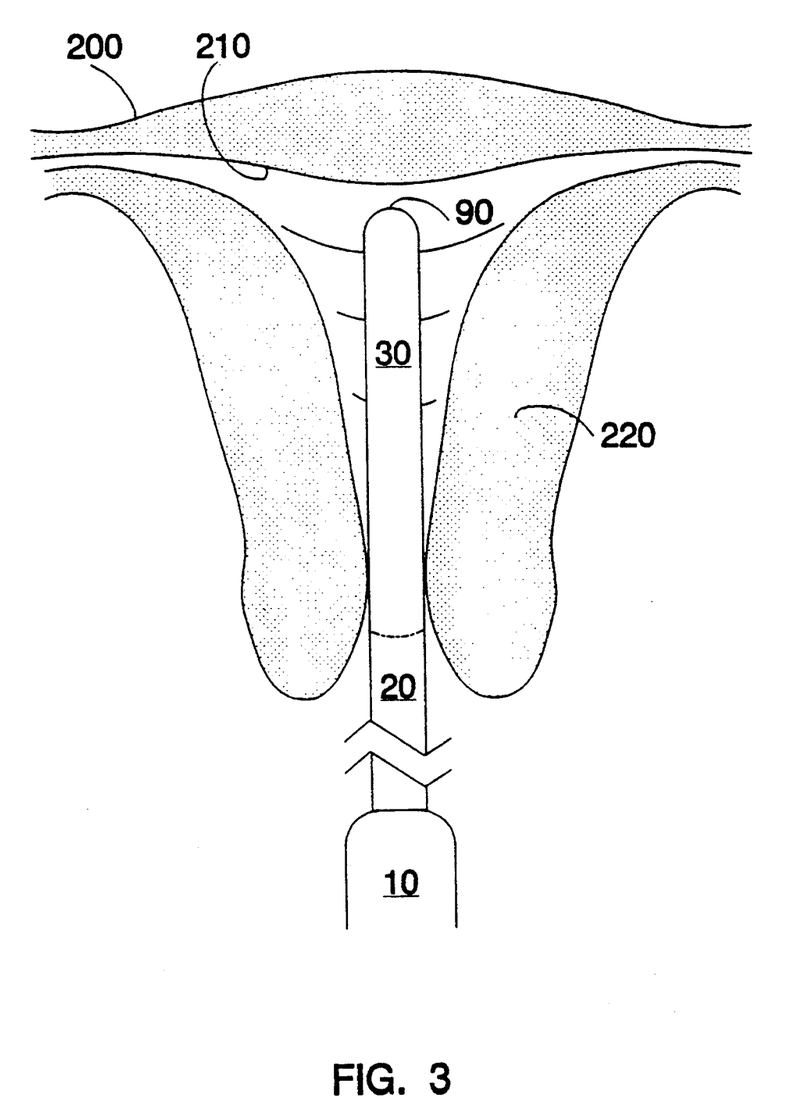
FIG. 3 illustrates the cryosurgical probe of FIG. 1 in place in a patient's uterus.

FIG. 3 is a schematic diagram showing the cryosurgical probe in place in a patient's uterus 200. The cryosurgical probe can be used in a surgical procedure to remove the endometrium, which is a thin layer of cells on the interior surface 210 of the muscular walls 220 of the uterus.

The probe is inserted into the uterus through the patient's vagina and cervical canal. The rounded end and flattened, tapering cross section of the cooling tip 30, along with the straight shaft 20, assist the surgeon to pass the probe along the vagina, through the cervix and into the uterine cavity. The surgeon relies on feel and experience to position the probe. He may also employ a vaginal speculum so that he can pass the probe through the cervix under visual guidance.

Once the cooling tip 30 of the cryosugical probe is correctly positioned within the uterus 200, and before any cooling of the cooling tip 30 is performed, the surgeon depresses the plunger 100 of the syringe 60 mounted on the handle portion 10 of the cryosurgical probe. This causes the isotonic solution 70 to be forced out of the aperture 90 into the interior of the uterus 200. The interior of the uterus is distended with about 5 millilitres of isotonic solution. The surgeon then stops pressing the plunger 100 and operates a valve to supply high pressure gas through the gas inlet 40, along the tube 120 to the nozzle 130. He also opens the exhaust vents from the cooling tip 30. According to the mechanism described above, this causes the cooling tip 30 to be rapidly cooled, which in turn starts to freeze the isotonic solution in the interior of the uterus.

The cooling operation is continued until the ice formed around the cooling tip 30 extends to the interior 210 of the walls of the uterus 200. The formation of an ice block around the cooling tip 30 can be observed by the surgeon using a conventional ultrasound scanning device of the type used to observe an unborn foetus in the uterus. The formation of a block of ice of sufficient size to reach the walls of the uterus may take about 10 minutes. The surgeon then continues the cooling operation in order to supercool the ice block down to about $-30°$ C. to $-45°$ C. (as measured by the thermocouple). The supercooled ice in contact with the endometrium has the effect of killing (ablating) the cells of the endometrium.

When the surgeon considers that ablation of the endometrium is complete, he operates a valve to close the exhaust vents from the cooling tip. As described above, the gas pressure in the region 140 builds up to $5 \times 10^6$ Pascals, and the interior walls of the cooling tip are warmed by the latent heat of condensation of the high pressure gas. Sufficient reheating is applied in this way in order to free the cooling tip 30 and the shaft 20 from the ice block formed in the interior of the uterus 200. The cryosurgical probe may then be withdrawn, leaving the majority of the ice block still in place. This ice block melts rapidly, well before the patient recovers from her anaesthesia.

The surgical procedure described above can be carried out under local or general anaesthetic and is minimally invasive. It is envisaged that the operation will require no more than an overnight stay in hospital for a patient; this compares with a typical seven-day stay in hospital for patients undergoing hysterectomies.

Figure 4:
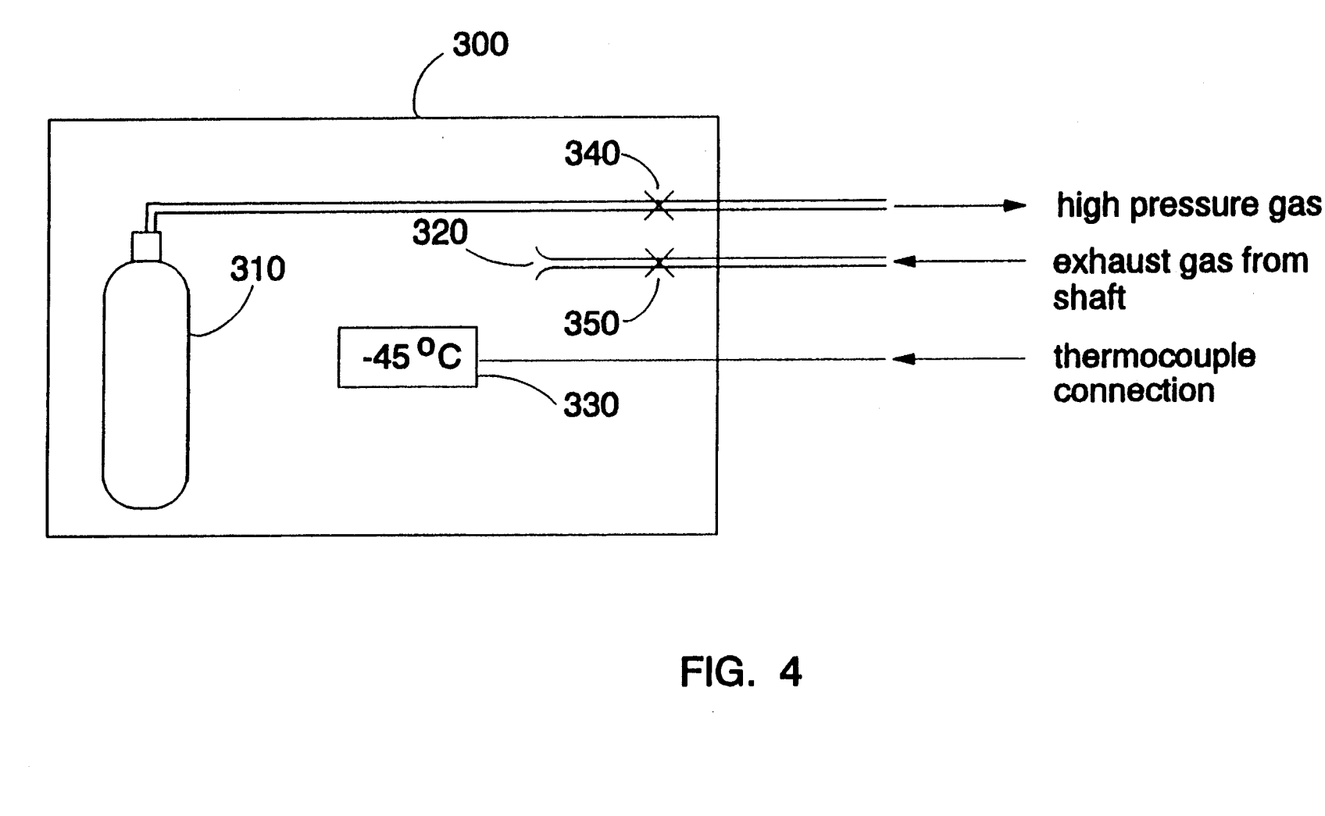
FIG. 4 is a schematic diagram of a control unit for controlling operation of the cryosurgical probe.

FIG. 4 is a schematic diagram of a control unit 300 for controlling operation of the cryosurgical probe. The control unit comprises a gas cylinder 310 for supplying high pressure gas to the gas inlet 40, an atmospheric air vent 320 connectable to the inner chamber 25 of the shaft 20 to receive exhaust gas from the region 140, and a temperature display device 330 connectable to the thermocouple temperature sensor 150. The gas cylinder 310 and the atmospheric air vent 320 are connected to the gas inlet 40 and the gas outlet 45 respectively by flexible tubing. A valve 340 controls the flow of gas from the gas cylinder 310 to the gas inlet 40, and a valve 350 controls the flow of exhaust gas from the gas outlet vent. The valves 340 and 350 may be controlled by respective foot-switches (not shown).

In order to initiate cooling of the cooling tip 30, both of the valves 340 and 350 are opened. High pressure gas expands through the nozzle 130 into the region 140, cooling the cooling tip 30, and exhausts through the atmospheric air vent 320. When re-heating is required, the valve 350 is closed, shutting off the atmospheric air vent 320. The region 140 reaches a high gas pressure and the cooling tip is re-heated by latent heat of condensation.

Figure 5:
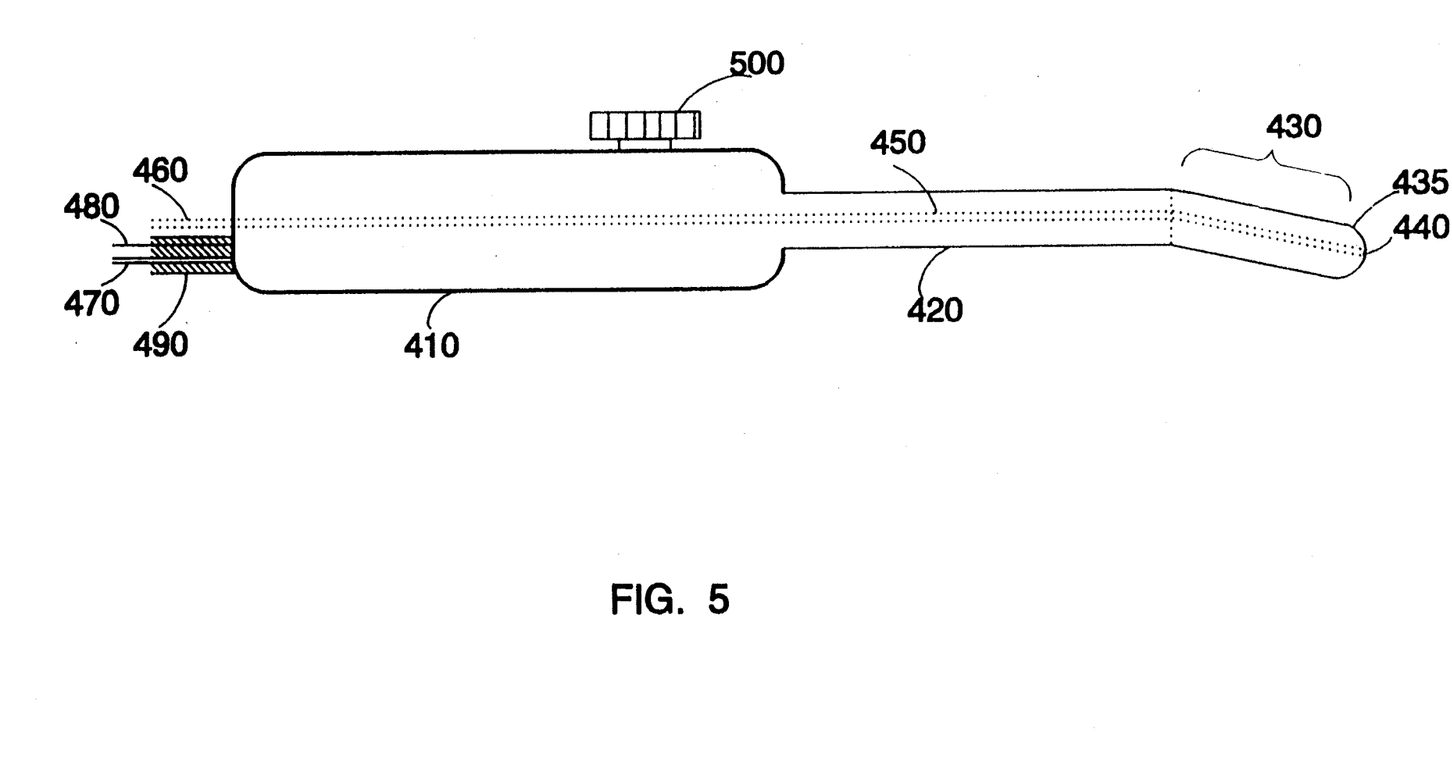
FIG. 5 is a schematic diagram of a second embodiment of a cryosurgical probe.

FIG. 5 is a schematic diagram of a second embodiment of a cryosurgical probe. The probe shown in FIG. 5 is similar to that shown in FIG. 1 and comprises a handle portion 410, a parallel sided cylindrical shaft 420 and a cooling tip 430. For ease of manufacturing, the cooling tip 430 is a parallel sided cylindrical element disposed at a slight angle to the shaft 420. The cooling tip 430 has a hemispherical distal end.

An aperture 440 is connected via a longitudinal channel 450 to an isotonic fluid inlet 460 at the proximal end of the handle portion 410. A high pressure gas inlet 470 and control wires 480 connected to a thermocouple (not shown) in the cooling tip 430 are disposed within a low pressure exhaust gas outlet tube 490.

The handle portion 410 comprises a pressure balancing valve controlled by a thumb wheel 500, to selectively block the exhaust of gas from the cooling tip 430. The pressure balancing valve 500 will be described in further detail below with reference to FIG. 6.

The use of a control valve on the handle 410, to selectively block the exhaust of gas from the cooling tip 430, removes the requirement for a high pressure exhaust gas tube from the handle to the control unit 300. In fact, as shown in FIG. 5, a wide bore, low pressure tube 490 can be employed. The use of a larger exhaust passage reduces the back pressure at the cooling tip during a cooling operation; this in turn allows a more efficient cooling operation to take place and a lower tip temperature (e.g. −80° C.) to be achieved.

Figure 6:
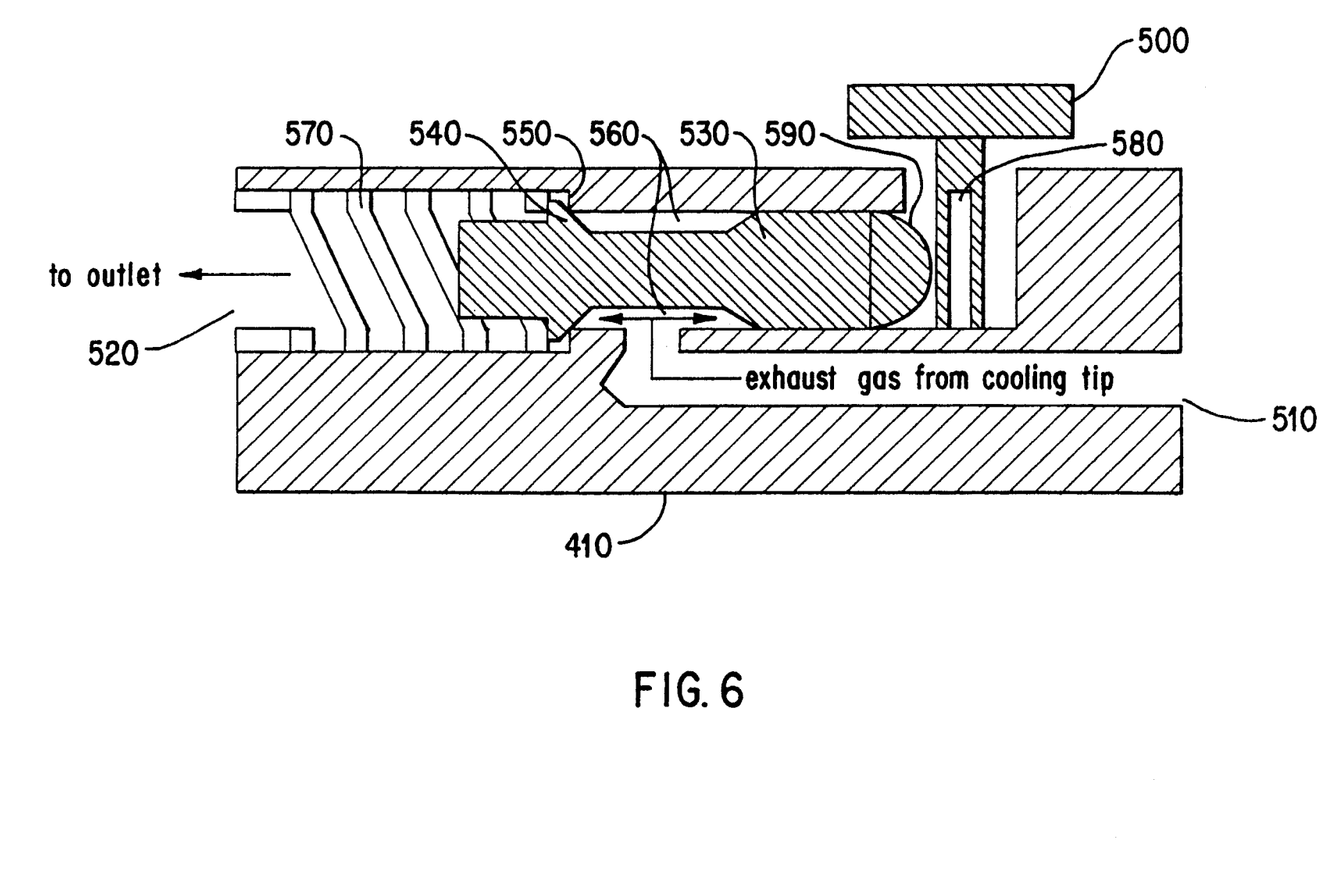
FIG. 6 is a schematic diagram of a pressure balancing valve.

FIG. 6 is a schematic diagram of a pressure balancing valve employed in the handle portion 410 of the probe shown in FIG. 5.

In FIG. 6, a high pressure exhaust gas passage 510 carries exhaust gas from the cooling tip 430, and a low pressure exhaust gas outlet 520 communicates with the exhaust tube 490 to carry exhaust gases to the control unit 300.

The pressure balancing valve is shown in FIG. 6 in its closed position. In this position, a plunger 530 having a deformable sealing ring 540 forms a seal against a stepped portion 550 of the casing of the handle 410. In an open position (not shown), the plunger is moved to the left so that a gap is formed between the sealing ring 540 and the stepped portion 550.

In the closed position, the high pressure exhaust gas passage 510 is connected to a chamber 560 formed by indentations on the plunger 530. High pressure gas in the chamber 560 then exerts an equal and opposite pressure on the plunger in each horizontal direction. This balancing of pressures in an opening and closing direction means that the valve can be held closed by a light spring 570, and that a relatively small force is required to open the valve. This makes the valve suitable for manual opening and closing, despite the high gas pressures involved.

In order to open the valve, the thumb wheel 500 is turned which causes a cam surface 580 to press the end 590 of the plunger 530 against the spring pressure 570. As mentioned above, this causes a gap to be formed between the sealing ring 540 and the stepped portion 550. Exhaust gas may then pass from the high pressure tube 510 to the low pressure exhaust outlet 520.

A detent mechanism (not shown) is employed to hold the valve lightly in its closed position.

Although illustrative embodiments of the invention have been described in detail herein with reference to the accompanying drawings, it is to be understood that the invention is not limited to those precise embodiments, and that various changes and modifications can be effected therein by one skilled in the aft without departing from the scope and spirit of the invention as defined by the appended claims.

We claim:

1. A cryosurgical probe insertable into the interior of a bodily cavity for performing cryosurgical ablation on the interior of said cavity, said probe defining a channel for introducing a heat-conducting liquid into said cavity; and said probe comprising a cooling element for cooling said heat-conducting liquid in said cavity.

2. A probe according to claim 1, in which said cooling element defines a hollow chamber connectable to an exhaust vent, and comprises a gas nozzle connectable to a supply of gas at greater than atmospheric pressure.

3. A probe according to claim 2, comprising a valve for selectively blocking said exhaust vent.

4. A probe according to claim 1, in which said heat-conducting liquid comprises an aqueous isotonic solution, said cooling element being operable to freeze said aqueous isotonic solution.

5. A probe according to claim 1, comprising means for detecting a temperature of said cooling element.

6. A probe according to claim 5, in which said means for detecting temperature comprises a thermocouple sensor in said cooling element.

7. A probe according to claim 1, in which:
said probe comprises a substantially cylindrical elongate body, and
said cooling element comprises an elongate cooling tip attached to one end of said elongate body.

8. A probe according to claim 7, in which:
said elongate body has a principal axis;
said cooling tip has a principal axis;
said principal axes of said elongate body and said cooling tip are not parallel; and
said cooling tip is joined to said elongate body by a smoothly curved transition.

9. A probe according to claim 7, in which a distal end of said cooling tip has a rounded shape.

10. A probe according to claim 7, in which said cooling tip is tapered and has a flattened cross section.

11. A probe according to claim 7, in which said elongate body has a double-walled structure.

12. A probe according to claim 1, comprising a syringe, connected to said channel, for supplying said heat-conducting liquid to said channel.

13. Cryosurgical ablation apparatus comprising:
a probe according to claim 2;
means for supplying gas to the probe at greater than atmospheric pressure.

14. A probe according to claim 3, comprising a handle portion, said handle portion comprising said valve for selectively blocking said exhaust vent.

15. A probe according to claim 14, comprising:
an inlet gas tube for supplying gas at greater than atmospheric pressure to said gas nozzle; and
an outlet gas tube for receiving gas from said exhaust vent;
said inlet gas tube having a narrower bore than said outlet gas tube.

16. A probe according to claim 14, in which said valve is a pressure-balancing valve.

17. A probe according to claim 14, comprising a detent mechanism for maintaining said valve in a blocking position.

18. A method of performing cryosurgical ablation on the interior of a bodily cavity, said method comprising the steps of:
introducing a heat-conducting liquid into said cavity; and
cooling said heat-conducting liquid in said cavity.

19. A method of performing cryosurgical ablation on the interior of a bodily cavity, said method comprising the steps of:
(i) introducing a cryosurgical probe into said cavity, said probe comprising a cooling element and said probe defining a channel communicating with said cavity;
(ii) introducing a heat conducting liquid into said cavity through said channel; and
(iii) cooling said cooling element to cool said heat conducting liquid in said cavity.

* * * * *